United States Patent [19]
Van Hale

[11] Patent Number: 5,342,196
[45] Date of Patent: Aug. 30, 1994

[54] DENTAL HAND PIECE

[76] Inventor: Gregory L. Van Hale, 247 W. Glenoaks, Glendale, Calif. 91202

[21] Appl. No.: 24,375

[22] Filed: Mar. 1, 1993

[51] Int. Cl.$^5$ .................. A61C 17/02; A61C 17/06
[52] U.S. Cl. .................................. 433/82; 433/91; 433/132
[58] Field of Search ............... 433/114, 116, 91, 132, 433/82

[56] References Cited

U.S. PATENT DOCUMENTS

| | | | |
|---|---|---|---|
| 3,014,278 | 12/1961 | Aymar et al. | 433/132 |
| 3,526,219 | 9/1970 | Balamuth | 433/91 |
| 3,646,678 | 3/1972 | McAlister | 433/91 |
| 4,176,453 | 12/1979 | Abbott | 433/91 |
| 4,253,831 | 3/1981 | Eaton, II | 433/116 |
| 4,917,603 | 4/1990 | Haack | 433/91 |
| 4,941,828 | 7/1990 | Kimura | 433/132 |
| 5,122,153 | 6/1992 | Harrel | 433/114 |

Primary Examiner—Cary E. O'Connor
Attorney, Agent, or Firm—James E. Brunton

[57] ABSTRACT

An aspirating dental hand piece having at its distal end a vacuum scoop that circumscribes the work tool and automatically carries away cooling water and debris during operation of the hand piece. The hand piece includes a two-part handle. The distal portion of the handle terminates in a suction scoop or shroud within which the gas driven motor is housed. This portion of the handle is divided into two portions, one of which houses the cooling fluid, gas and fiber optic conduits, and the other of which forms a fluid passageway in communication with the suction scoop for carrying away the cooling fluid and the debris generated during the drilling and grinding operations. The fluid and debris passageway is sealed with respect to the conduit carrying portion of the handle.

10 Claims, 3 Drawing Sheets

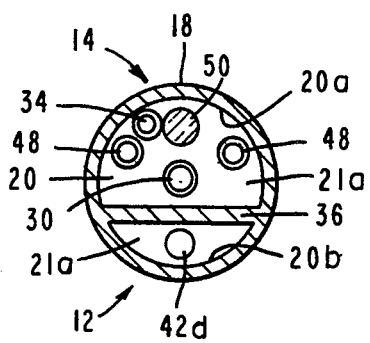
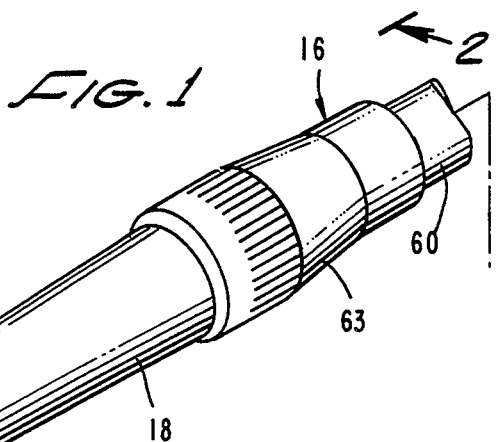
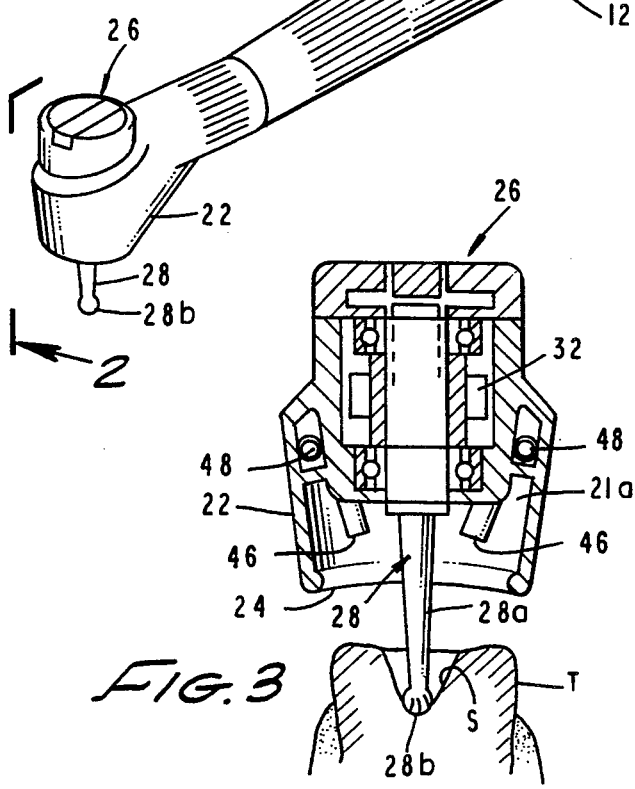
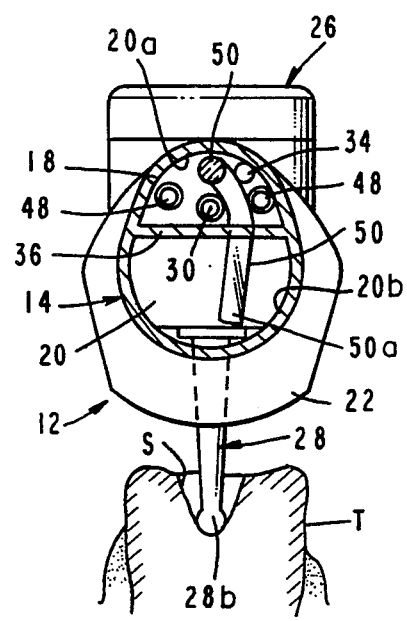
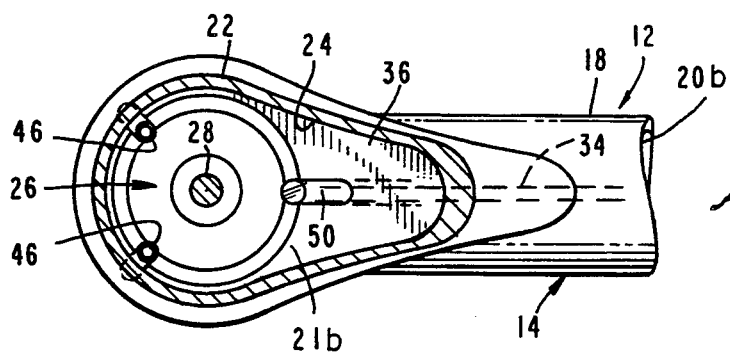

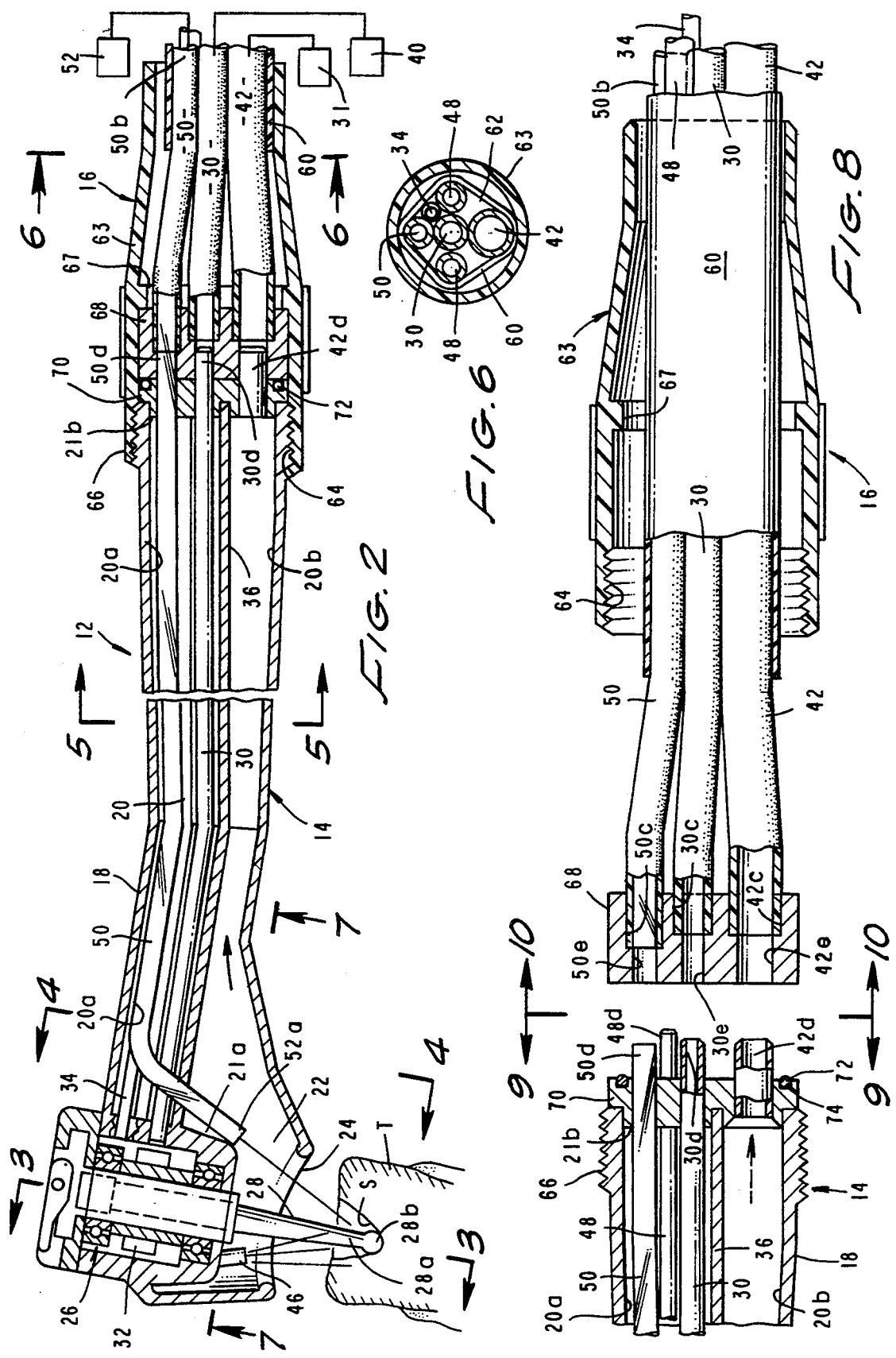

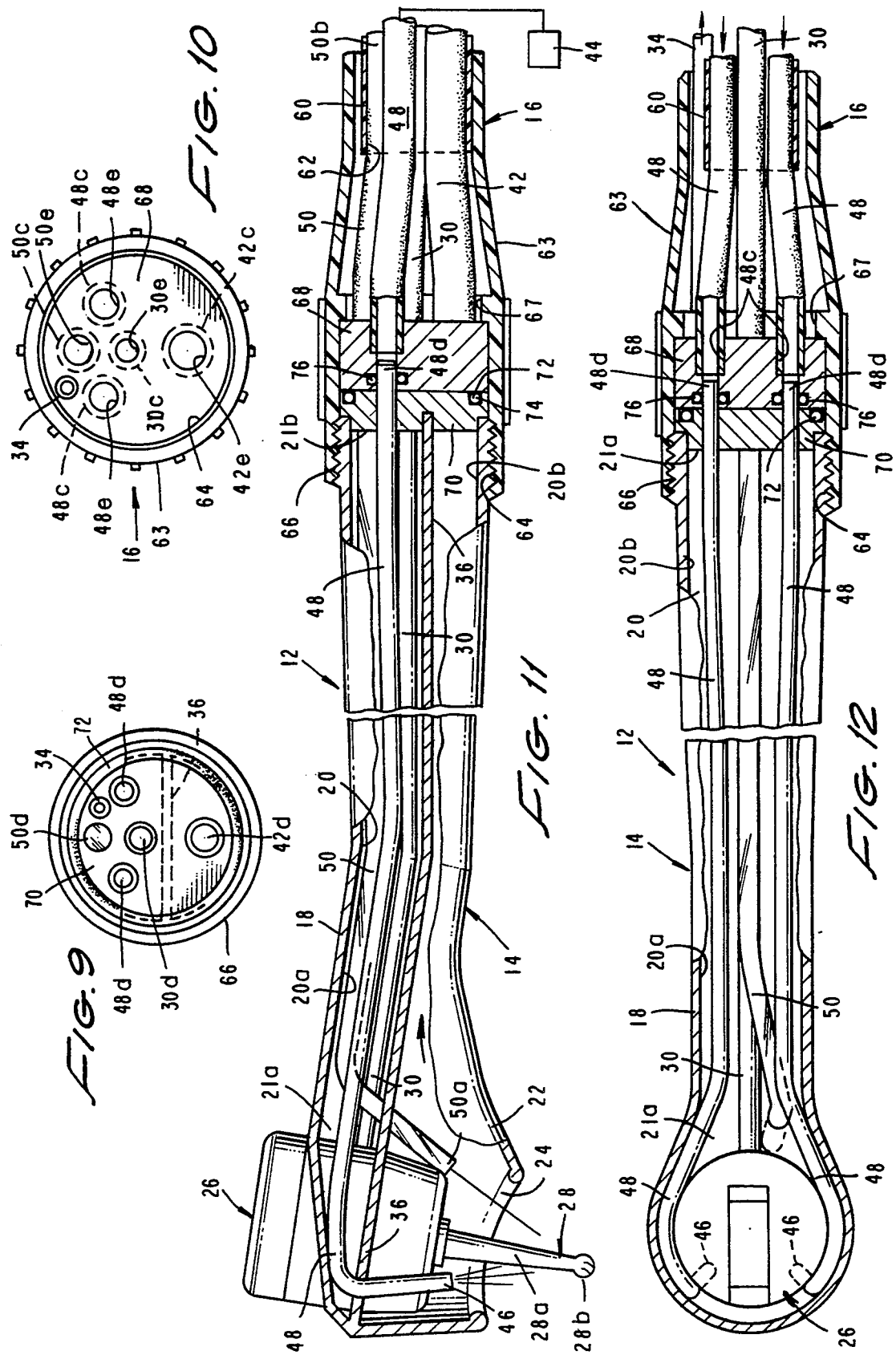

DENTAL HAND PIECE

BACKGROUND OF THE INVENTION

Field of the Invention

The present invention relates generally to dental hand pieces. More particularly, the invention concerns an aspirating dental hand piece having at its distal end a vacuum scoop that circumscribes the work tool and automatically carries away cooling water and debris during operation of the hand piece.

Discussion of the Invention

High speed gas driven dental hand pieces are well known in the prior art. Typically such hand pieces include a gas driven motor provided at the distal end of a handle for driving a work tool at high speeds of rotation. During operation of the hand piece, it is necessary to direct a cooling fluid toward the work tool to cool it and the work site and to wash away tooth debris formed during performance of the dental procedure.

In the past, separate aspiration or suction devices have been used to collect the cooling fluid and debris and carry it away from the work site. Generally these devices include an elongated tube having a suction nozzle at one end which is disposed within the patient's mouth proximate the tooth being worked on. These suction devices are generally unwieldy and must be operated by the dental assistant as the dentist performs the dental procedure using the dental hand piece. Accordingly, two people, that is the dentist and the dental assistant, must both be present during the dental procedure.

The present invention overcomes this significant drawback by providing as an integral part of the dental hand piece itself, a suction means for automatically carrying away the cooling water and the dental debris generated during the performance of the dental procedure. Since the dentist is manipulating the hand piece along with the built-in suction means, the dental assistant is not needed and can be performing other important work such as sterilization in accordance with recent OSHA procedures.

The hand piece of the present invention includes a two-part handle. The distal portion of the handle terminates in a suction scoop or shroud within which the gas driven motor is housed. This portion of the handle is uniquely divided into two portions, one of which houses the cooling fluid, gas and fiber optic conduits, and the other of which forms a fluid passageway in communication with the suction scoop for carrying away the cooling fluid and the debris generated during the drilling and grinding operations. Due to the unique design of the suction means of the invention, greater amounts of water than normal can be used to ease the cutting process. The fluid and debris passageway is sealed with respect to the conduit carrying portion of the handle. The proximal portion of the handle, which is removably interconnected with the distal portion by appropriate coupling means, carries the cooling fluid, gas, vacuum and fiber optic input conduits which are, in turn, interconnectable with the conduits carried by the distal portion of the handle upon mateably interconnecting the two portions of the handle.

U.S. Pat. No. 4,203,221 issued to Knop et al discloses a two part dental hand piece and includes resilient means forming a portion of the means for interconnecting the two parts of the handle. This patent nowhere discloses or suggests the novel suction means of the apparatus of the present invention.

U.S. Pat. No. 4,249,896 issued to Kerfoot, Jr. discloses a gas driving dental hand piece having decreased noise and improved vibration damping characteristics. Kerfoot also fails to disclose or suggest any type of integral vacuum system of the character disclosed herein.

SUMMARY OF THE INVENTION

It is an object of the present invention to provide a dental hand piece which includes an integral suction system for automatically carrying away from the work site cooling water and debris generated during the performance of the dental procedure.

More particularly, it is an object of the invention to provide a dental hand piece of the aforementioned character in which the gas driven motor which drives the work tool is housed within a downwardly depending shroud that uniquely functions as a suction scoop for automatically capturing the cooling water which cools the work site and the debris, including tooth debris, saliva, blood and like materials which are formed during drilling and grinding of the patient's tooth.

Another object of the invention is to provide a dental hand piece and integral suction system which can be operated by the dentist using one hand without the aid of a dental assistant thereby decreasing the number of people exposed to any pathogens encountered during the operating procedure.

Another object of the invention is to provide a device of the character described in the preceding paragraphs which includes built-in illumination means for illuminating the work area.

Another object of the invention is to provide a hand piece as described which is compact, light weight, easy to use and easy to clean and sterilize.

Still another object of the invention is to provide a combined hand piece and suction unit which includes readily interconnectable distal and proximal portions, the distal portion being divided into two portions one of which comprises a fluid passageway for carrying away the cooling fluid and the dental debris.

Yet another object of the invention is to provide a dental hand piece of the class described that is compatible with standard sources of compressed gas, vacuum and electrical power.

Another object of the invention is to provide an apparatus as described which decreases the amount of airborne particles, aerosols and other contaminates which may be generated during the operating procedure.

Another object of the invention is to provide a dental hand piece of the character described in the preceding paragraphs which is of simple design for ease of manufacture and one which can be inexpensively produced in large volume.

BRIEF DESCRIPTION OF THE DRAWINGS

FIG. 1 is a generally perspective view of one form of the aspirating hand piece of the invention.

FIG. 2 is a cross-sectional view taken along lines 2—2 of FIG. 1.

FIG. 3 is a cross-sectional view taken along lines 3—3 of FIG. 2.

FIG. 4 is a cross-sectional view taken along lines 4—4 of FIG. 2.

FIG. 5 is a cross-sectional view taken along lines 5—5 of FIG. 2.

FIG. 6 is a cross-sectional view taken along lines 6—6 of FIG. 2.

FIG. 7 is a view taken along lines 7—7 of FIG. 2.

FIG. 8 is an exploded side elevational, cross-sectional view similar to FIG. 2 but showing the rearward portion of the apparatus separated from the forward operating portion.

FIG. 9 is a view taken along lines 9—9 of FIG. 8.

FIG. 10 is a cross-sectional view taken along lines 10—10 of FIG. 8.

FIG. 11 is a side elevational view similar to FIG. 2 showing the routing of the cooling water conduit.

FIG. 12 is a top cross-sectional view further illustrating the routing of the cooling water conduit and the light conducting fiber optic conduit.

DESCRIPTION OF THE INVENTION

Referring to the drawings and particularly to FIGS. 1 and 2, the aspirating dental hand piece system of the present invention comprises an elongated handle assembly 12 made up of first and second releasably interconnected handle members 14 and 16 which are constructed of a suitable metal such as stainless steel or the like. First handle member 14 includes an outer wall 18 defining an interior space 20 having first and second ends 20a and 20b. First or distal end 20a terminates in intake means shown here as a downwardly depending shroud or scoop-like portion 22 having an open mouth 24. A gas driven motor 26 is carried at the distal end of handle member 14 and is adapted to rotatably drive a work tool 28 at very high speeds of rotation. Gas driven motor 26 is driven in conventional fashion by a gas under pressure such as air carried by a gas conduit 30 which is interconnected with a source of compressed gas 31. Motor 26 is of a conventional design well known to those skilled in the art and readily available from a number of manufacturers including KaVo America Corporation of Hoffman Estates, Illinois. Work tool 28 is driven by the gas turbine portion 32 of gas motor 26 with exhaust gases being carried away from the turbine by an exhaust conduit 34 which extends through the handle assembly and appropriately exhausts to atmosphere at the proximal end of the handle assembly. Work tool 28 includes an elongated shank 28a which extends from mouth 24 and terminates in a grinding burr 28b.

Referring to FIG. 5, an important feature of the present invention resides in the provision of a transversely-extending interior dividing wall 36 which is connected to outer wall 18 internally of handle member 14. Wall 36 uniquely divides interior space 20 into upper and lower, or first and second, portions designated in FIG. 5 by the numerals 20a and 20b. As best seen in FIG. 2, portion 20b of the interior space is operably inter connected with vacuum means including a vacuum source such as vacuum pump 40 of standard construction. Pump 40, which is interconnected with space 20b by means of an elongated conduit 42, is adapted to create a vacuum within chamber 20b that is sufficient to capture and channel into interior portion 20b cooling water and debris generated during the grinding and drilling of the patient's tooth T.

In order to cool the work tool 28 and the work site S formed in tooth T, fluid cooling means are provided. The fluid cooling means here comprises a source of cooling fluid 44 (FIG. 11), which is preferably cool water. A pair of fluid spray jets 46 are mounted within shroud portion 22 for controllably directing the cooling water toward the work tool and the work site S. Also comprising a part of the cooling means are water carrying conduits 48 (FIG. 12) which extend through the handle assembly and function to appropriately interconnect the source of cooling water with spray jets 46 which are mounted distally with respect to work tool 28.

In the embodiment of the invention shown in the drawings, there is also provided illumination means for illuminating the work tool and the work site. The illumination means is here provided in the form of a multiplicity of optic fibers contained within an optic fiber conduit 50, one end 50a of which is disposed proximate mouth 24 of shroud 22 and the other end 50b of which is interconnected with a suitable source of illumination such as a light 52 (FIG. 2). Both the source of light and the fiber optic conduits are of a character well known to those skilled in the art.

An important feature of the apparatus of the present invention resides in the fact that the compressed gas conduits, cooling water conduits, and the optic fiber conduits and the exhaust conduit are all disposed within the sealed upper interior space 20a of the distal end piece member 14 (FIG. 4). Because all of the utility conduits are housed within the upper interior space 20a of the distal handle member, interior space 20b of the handle is free and open so as to efficiently conduct away from the work site excess cooling water and grinding debris resulting from the dental procedure. Since the upper and lower interior spaces 20a and 20b are separated by divider wall 36, the fiber optic, gas, and cooling water conduits are protected from contamination which might be caused by the cooling water and debris flowing through space 20b of the forward hand piece member 14.

Turning now to FIGS. 6 through 12, second handle member 16 includes an outer wall 60 which defines an interior space 62. Slidably mounted over Wall 60 is a connector ring 63 which is provided with internal threads 64 disposed proximate its inboard end. Threads 64 are adapted to mate with external threads 66 provided on first handle portion 14. Threads 66 along with ring 63 comprise the connector means of the present form of the invention for interconnecting the first and second handle members 14 and 16. As best seen by referring to FIG. 6, the various utility conduits which carry the cooling water, vacuum compressed gas and fiber optics are all contained within internal space 62 and extend therefrom at the proximal end of the handle assembly for appropriate interconnection with the various sources of supply (FIGS. 2 and 11).

As best seen in FIGS. 11 and 12, disposed internally of ring 63 is an end wall 68 which sealably abuts an end wall 70 which closes interior space 20a and 20b of the first handle member 14. When threads 64 and 66 are mated an internal step 67 provided within ring 63 urges walls 68 and 70 into close proximity. An elastomeric O ring 72 which is disposed in an O ring groove 74 provided in end wall 70 prevents fluid leakage between the walls. As best seen by also referring to FIGS. 8 and 10, each of the utility conduits 30, 42 and 50 are received within spaced-apart bores 30c, 42c and 50c provided in end wall 68. In the manner shown in FIG. 8. Similarly, as indicated in FIG. 12, fluid conduits 48 are received within spaced-apart bores 48c provided in wall 68. As depicted in FIGS. 8 and 10, portions 30d, 42d, 48d and 50d respectively of the utility conduits 30, 42, 46 and 50 extend through wall 70 so that the end portions thereof can be received within reduced diameter bores 30e, 42e, 48e and 50e respectively provided in wall 68 which bores communicate with the utility conduits 30, 42, 48 and 50. As indicated in FIG. 12, elastomeric O rings 74 which are carried in O ring grooves provided in end wall 68 sealably engage end portions 48d of fluid conduits 48 so as to prevent fluid leakage between the conduits and end wall 68. With the construction thus described, when handle members 14 and 16 are interconnected by ring 63, the various utility conduits mate in the manner shown in the drawings to provide fluid flow paths between the utility sources and the distal portion of the handle assembly. It is apparent that by rotation of ring 63, the distal and proximal portions of the handle assembly can be quickly and easily disconnected so that the distal or forward portion of the handle assembly can be appropriately cleaned, and maintained.

In using the aspirating dental hand piece system of the present invention, the distal and proximal portions of the handle assembly are first threadably interconnected in the manner shown in FIG. 2. This renders the hand piece operable and the gas motor 26, the illumination means and the vacuum pump can be energized. Upon starting the flow of the cooling water, the device is used in a standard manner to perform the dental procedure. However, because of the unique design of the device, it is apparent that, when the device is in the position shown in FIG. 2, the vacuum source will create a sufficient negative pressure at the mouth 24 and within passageway 22 to cause the cooling water and the dental debris generated by the work tool to be sucked into mouth 24 and thence rearwardly of the distal hand piece and through interior space 20b of the distal portion of the hand piece to a suitable receptacle. The unique design of shroud 22 and open mouth 24 insures that during normal grinding and drilling procedures the cooling water and debris will automatically be removed from the work site without the need for auxiliary suction devices of the character normally operated by the dental assistant.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim

1. An aspirating dental hand piece system comprising:
   (a) an elongated first handle member including:
      (i) an outer wall defining an interior space having first and second ends, said first end terminating in a downwardly depending shroud having an open mouth;
      (ii) a gas driven motor connected to said outer wall proximate said first end of said interior space;
      (iii) a work tool rotatably driven by said motor, said work tool having a shank portion extending from said open mouth of said shroud;
      (iv) cooling means, including a source of cooling fluid, for directing a cooling fluid outwardly of said open mouth of said shroud toward said shank portion, said cooling means comprising a spray jet disposed within said shroud and a fluid conduit disposed within said shroud and a fluid conduit disposed within said interior space of said first handle member, one end of said fluid conduit being in communication with said spray jet and the other end being in communication with said source of cooling fluid;
      (v) a divider wall connected to said outer wall for dividing said interior space of said first handle member into first and second portions, said second portion being in communication with said shroud; and
      (vi) vacuum means including a vacuum source for producing a vacuum within said second portion tending to urge said cooling fluid to flow inwardly into said second portion; and
   (b) an elongated second handle member removably connected to said first handle member, said second handle having an outer wall defining an interior space and connector means for interconnecting said first and second handle members.

2. A system as defined in claim 1 further including illuminating means for illuminating said shank portion of said work tool.

3. A system as defined in claim 2 in which said illuminating means comprises a first fiber optic conduit extending through said interior of said second handle member and a second fiber optic conduit connected to said first optic conduit and extending through said first portion of said interior space of said first handle member.

4. As aspirating dental hand piece system for use in grinding a patient's tooth comprising:
   (a) an elongated first handle member including:
      (i) an outer wall defining an interior space having first and second ends, said first end terminating in a downwardly depending shroud having an open mouth;
      (ii) a gas driven motor connected to said outer wall proximate said first end of said interior space;
      (iii) a work tool rotatably driven by said motor, said work tool having a shank portion extending from said open mouth of said shroud;
      (iv) cooling means, including a source of cooling fluid for directing a cooling fluid outwardly of said open mouth onto the tooth said cooling means comprising a pair of spray jets disposed within said shroud and a pair of fluid conduits disposed within said interior space of said second handle member one end of each said fluid conduit being in communication with one of said spray jets and the other end of each said fluid conduit being in communication with said source of cooling fluid; and
      (v) a divider wall connected to said outer wall for dividing said interior space into first and second portions comprising a fluid passageway in communication with said shroud;
   (b) an elongated second handle member removably connected to said first handle member, said second handle including:
      (i) an outer wall defining an interior space; and
      (ii) a vacuum conduit carried within said interior space;
   (c) connector means for releasably interconnecting said first and second handle members so that said vacuum conduit is in communication with said fluid passageway of said first handle means; and (d) vacuum means including a vacuum pump connected to said vacuum conduit for producing a vacuum within said vacuum conduit and said fluid passageway sufficient to urge said cooling fluid flowing onto the tooth to then flow inwardly into said mouth of said shroud.

5. A system as defined in claim 4 further including illuminating means for illuminating the tooth.

6. A system as defined in claim 4 further including an exhaust conduit connected to said motor and extending through said interior space of said first and second handle members.

7. An aspirating dental hand piece system comprising:
 (a) a first handle member including:
  (i) an outer wall defining an interior space having first and second ends, said first end terminating in a downwardly depending shroud having an open mouth;
  (ii) a motor connected to said outer wall proximate said first end of said interior space;
  (iii) a work tool rotatably driven by said motor, said work tool having a shank portion extending from said open mouth of said shroud;
  (iv) cooling means, including a source of cooling fluid, for directing a cooling fluid outwardly of said open mouth of said shroud toward said shank portion, said cooling means comprising a spray jet disposed within said shroud and a fluid conduit disposed within said interior space of said second handle member, one end of said fluid conduit being in communication with said spray jet and the other end being in communication with said source of cooling fluid;
  (v) vacuum means including a vacuum source for producing a vacuum tending to urge said cooling fluid to flow inwardly into said interior space; and
 (b) a second handle member connected to said first handle member, said second handle having an outer wall defining an interior space and connector means for interconnecting said first and second handle members.

8. A system as defined in claim 7 in which said vacuum means comprises a vacuum conduit disposed within said interior space of said second handle member one end of said conduit being in communication with said vacuum source.

9. A system as defined in claim 7 further including illuminating means for illuminating the tooth.

10. A system as defined in claim 7 in which said motor is gas driven and in which said system further includes an exhaust conduit connected to said motor and extending through said interior space of said first and second handle members.

* * * * *